United States Patent [19]

Kasch et al.

[11] Patent Number: 5,407,928
[45] Date of Patent: Apr. 18, 1995

[54] 11β-ARYL-GONA-4,9-DIEN-3-ONES

[75] Inventors: Helmut Kasch; Gudrun Bertram; Kurt Ponsold; Gerd Schubert; Heidemarie Röhrig; Anatoli Kurischko; Bernd Menzenbach, all of Jena, Germany

[73] Assignee: Schering Aktiengesellschaft, Berlin and Bergkamen, Germany

[21] Appl. No.: 153,558

[22] Filed: Nov. 17, 1993

Related U.S. Application Data

[63] Continuation of Ser. No. 769,271, Oct. 1, 1991, abandoned, which is a continuation of Ser. No. 567,368, Aug. 15, 1990, abandoned.

[51] Int. Cl.⁶ .................................................. C07J 1/00
[52] U.S. Cl. .................................. 514/179; 552/648; 552/514; 552/610
[58] Field of Search ............... 514/179; 552/514, 610, 552/648

[56] References Cited

U.S. PATENT DOCUMENTS 4,609,651  9/1986  Rohde et al. .................... 514/179

FOREIGN PATENT DOCUMENTS

| | | |
|---|---|---|
| 0097572 | 1/1984 | European Pat. Off. . |
| 0104387 | 4/1984 | European Pat. Off. . |
| 0110434 | 6/1984 | European Pat. Off. . |
| 0129499 | 12/1984 | European Pat. Off. . |
| 0135400 | 3/1985 | European Pat. Off. . |
| 0147361 | 7/1985 | European Pat. Off. . |
| 0184471 | 6/1986 | European Pat. Off. . |
| 0190759 | 8/1986 | European Pat. Off. . |
| 0254670 | 1/1988 | European Pat. Off. . |
| 0277676 | 8/1988 | European Pat. Off. . |
| 0289073 | 11/1988 | European Pat. Off. . |
| 0299913 | 1/1989 | European Pat. Off. . |
| 0305242 | 3/1989 | European Pat. Off. . |
| 0308345 | 3/1989 | European Pat. Off. . |
| 0321010 | 6/1989 | European Pat. Off. . |
| 2586021 | 2/1987 | France . |
| 2160873 | 1/1986 | United Kingdom . |
| 8303099 | 9/1983 | WIPO . |
| 8912448 | 12/1989 | WIPO . |

*Primary Examiner*—Johann Richter
*Assistant Examiner*—Kimberly J. Kestler
*Attorney, Agent, or Firm*—Millen, White, Zelano, & Branigan

[57] ABSTRACT

This invention relates to 11β-aryl-gona-4,9-dienes of the general formula I

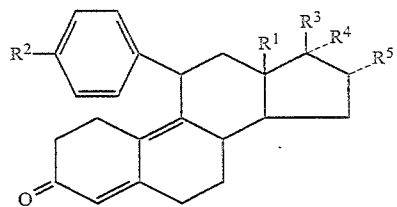

wherein the variables are defined in the specification. The compounds are progesterone antagonists and are suitable for inducing labor or an abortion.

5 Claims, No Drawings

11β-ARYL-GONA-4,9-DIEN-3-ONES

This application is a continuation of application Ser. No. 07/769,271, filed Oct. 1, 1991, now abandoned, which is a continuation of Ser. No. 07/567,368, filed Aug. 15, 1990, now abandoned.

This invention relates to 11beta-aryl-gona-4,9-dienes of general formula I

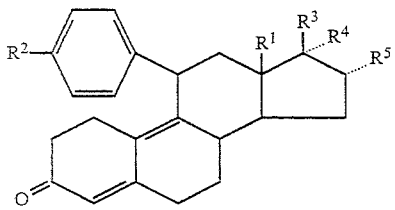

in which
A)
R$^1$ means a methyl group or ethyl group,
R$^2$ means an alkoxy group, alkylthio group, and by alkyl is to be understood an alkyl compound, alkenyl compound or a corresponding cyclic compound with 1 or 2 or 3 to 7 carbon atoms, a dimethylamino group, monomethylamino group, cyano group, formyl group, acetyl group of 1-hydroxyethyl group,
R$^3$ means a hydroxy, alkoxymethoxy, alkanoyloxy or alkoxy group with 1 to 6 carbon atoms each, and
R$^4$ means an ethinyl, prop-1-inyl, 3-hydroxyprop-1-inyl, 3-alkanoyloxyprop-1-inyl, 3-alkanoyloxyprop-1-enyl, 3-alkanoyloxypropyl group with 1 to 6 carbon atoms each, 3-hydroxyprop-1-enyl and 3-hydroxypropyl group as well as
R$^5$ means a hydrogen atom or
B)
R$^1$ means a methyl group or ethyl group,
R$^2$ means a methoxy, thiomethyl, dimethylamino, monomethylamino, cyano, formyl, acetyl or 1-alkoxyethyl group with 1 to 6 carbon atoms in the alkoxy radical,
R$^3$ means a methyl, ethyl, formyl, acetyl, cyano, dimethyl-tert-butylsilyloxy, alkoxymethyl, alkoxy, 1-alkoxyethyl, alkoxymethyloxy, alkanoyloxyethyloxy group with 1 to 6 carbon atoms each in the alkoxy radical, and
R$^4$ means an ethinyl, prop-1-inyl, alkyl, 3-alkoxyprop-1-inyl, 3-alkoxyprop-1-inyl, 3-alkoxypropyl group with 1 to 4 carbon atoms each in the alkyl or alkoxy radical or the grouping —CH$_2$Y, in which Y means a cyano, azido or alkoxy radical with 1 to 6 carbon atoms as well as
R$^5$ means a hydrogen atom or a alkyl group with 1 to 4 carbon atoms or else
R$^4$ and R$^5$ together mean a methylene bridge or tetramethylene bridge or
C)
R$^1$ means a methyl group
R$^2$ means a dimethylamino, a free or ketalized acetyl group,
R$^3$ means an alkoxy group with 1 to 6 carbon atoms, an alkoxy or alkylthiomethyloxy group with 1 to 4 carbon atoms in the alkyl radical,
R$^4$ means an alkoxymethyl group with 1 to 6 carbon atoms in the alkoxy radical as well as R$^5$ means a hydrogen atom.
Preferably in this case there is meant by:
R$^1$ a methyl group
R$^2$ a dimethylamino or acetyl group and moreover in A)
R$^3$ a methoxy group
R$^4$ a prop-1-inyl, ethinyl, 3-hydroxy-prop-1-inyl, 3-hydroxy-prop-1(Z)-enyl, 3-hydroxypropyl group and
R$^5$ a hydrogen atom
in B)
R$^3$ a methoxy, acetyl or methoxymethyl group,
R$^4$ a prop-1-inyl, ethinyl or 3-hydroxypropyl group,
R$^5$ a hydrogen atom or
R$^4$ and R$^5$ together mean a methylene bridge or tetramethylene bridge or
in C)
R$^3$ a methoxy group,
R$^4$ a methoxymethyl, ethoxymethyl or propoxymethyl group and
R$^5$ a hydrogen.

Especially preferred are the following compounds of general formula I
11beta-(4-dimethylaminophenyl)-17beta-methoxy-17alpha-propinyl-13-ethyl-gona-4,9-dien-3-one,
11beta-(4-acetylphenyl)-17beta-methoxy-17alpha-propinyl-13-methyl-gona-4,9-dien-3-one,
11beta-(4-dimethylaminophenyl)-17beta-methoxy-17alpha-ethinyl-13-methyl-gona-4,9-dien-3-one,
11beta-(4-acetylphenyl)-17beta-methoxy-17alpha-ethinyl-13-methyl-gona-4,9-dien-3-one,
11beta-(4-acetylphenyl)-17alpha-(3'-hydroxy-1-propinyl)-17beta-methoxy-13-methyl-gona-4,9-dien-3-one,
11beta-(4-acetylphenyl)-17alpha-(3'-hydroxy-1'(Z)-propenyl)17-beta-methoxy-13-methyl-gona-4,9-dien-3-one as well as
11beta-(4-acetylphenyl)-17alpha-(3'-hydroxypropyl)-17beta-methoxy-13-methyl-gona-4,9-dien-3-one,
11beta-(4-acetylphenyl)-17beta-methoxy-16alpha,17alpha-methylene-estra-4,9-dien-3-one,
11beta-acetyl-17beta-(4-acetylphenyl)-16alpha,17alpha-cyclohexano-estra-4,9-dien-3-one,
11beta-(4-aceylphenyl)-16alpha,17alpha-cyclohexano-17beta-methoxymethyl-estra-4,9-dien-3-one,
11beta-(4-acetylphenyl)-17beta-methoxy-17alpha-methoxymethyl-estra-4,9-dien-3-one,
11beta-(4-dimethylminophenyl)-17beta-methoxy-17alpha methoxymethyl-estra-4,9-dien-3-one,
11beta-(4-acetylphenyl)-17alpha-ethoxymethyl-17beta-methoxy-estra-4,9-dien-3-one,
11beta-(4-acetylphenyl)-17beta-methoxy-17alpha-propoxymethyl-estra-4,9-dien-3-one,
11beta-(4-dimethylaminophenyl)-17beta-methoxy-17alpha-propinyl-13-methyl-gona-4,9-dien-3-one,
11beta-(4-methoxyphenyl)-17beta-methoxy-17alpha-propinyl-13-methyl-gona-4,9-dien-3-one,
11beta-(4-dimethylaminophenyl)-17alpha-(3'-hydroxy-1'-Z-propenyl)-17beta-methoxy-13-methyl-gona-4,9-dien-3-one,
11beta-(4-methoxyphenyl)-17beta-methoxy-17alpha-(3'-hydroxy-1'-Z-propenyl)-13-methyl-gona-4,9-dien-3-one,
11beta-(4-dimethylaminophenyl)-17alpha-(3'-hydroxypropyl)-17beta-methoxy-13-methyl-gona-4,9-dien-3-one, 11beta-(4-methoxyphenyl)-17alpha-(3'-hydroxy-
propyl)-17beta-methoxy-13-methyl-gona-4,9-dien-
3-one,
11beta-(4-dimethylaminophenyl)-17alpha-(3'-
hydroxy-1'-propinyl)-17beta-methoxy-13-methyl-
gona-4,9-dien-3-one,
11beta(4-methoxyphenyl)-17alpha-(3'-hydroxy-1'-
propinyl)-17beta-methoxy-13-methyl-gona-4,9-
dien-3-one,
11beta-(4-dimethylaminophenyl)-17alpha-ethinyl-
17beta-methoxy-13-methyl-gona-4,9-dien-3-one,
11beta-(4-methoxyphenyl)-17alpha-ethinyl-17beta-
methoxy-13-methyl-gona-4,9-dien-3-one,
11beta-(4-methoxyphenyl)-17beta-methoxy-17alpha-
methoxy methyl-13-methyl-gona-4,9-dien-3-one.

The compounds of general formula I have a strong affinity for the gestagen receptor, without themselves developing gestagen activity. They are competitive antagonists of progesterone (antigestagens); since they displace from the receptor the progesterone necessary for maintenance of pregnancy, they are suitable for triggering abortions and for inducing labor.

Besides said indications, the compounds according to the invention can also be used for treatment of endometriosis, dysmenorrhea and endocrine hormone-dependent tumors such as, e.g., breast cancer and meningioma.

The abortive action of the substances, determined by animal experiments, serves for characterizing the antigestagen action. For this purpose, female pregnant rats (positive sperm detection—b 1st day of pregnancy) weighing between 180 and 200 g were treated subcutaneously with the test compound, suspended in peanut oil, on the 5th to 8th day of pregnancy. After autopsy on the 20th day of pregnancy, the uteri were examined. In this case, the number of pregnant females and the average number of fetuses per pregnant animal was determined. The inhibitory effect was calculated as follows:

$$He = \left(1 - \frac{x_v \cdot n_k}{m_v \cdot x_k}\right) \cdot 100(\%)$$

x=number of pregnant females
n=number of impregnated females
v=test group
k=control group

| Group Substance | Total Dose (mg/animal/4 d) | N | Fertility absol. | Inhibition rel. % |
|---|---|---|---|---|
| 17beta-methoxy 17alpha-methoxy-methyl-11beta-acetylphenyl | 2 | 6 | 6 | 100 |
| 17beta-methoxy-17alpha-propinyl-11beta-acetylphenyl | 2 | 6 | 6 | 100 |
| 17beta-methoxy-16alpha,17alpha-methylene 11beta-acetylphenyl | 2 | 6 | 6 | 100 |
| 17beta-methoxy-17alpha-propinyl 11beta-dimethylaminophenyl | 2 | 6 | 6 | 100 |
| 17beta-methoxy-17alpha-ethinyl-11beta-acetylphenyl | 2 | 6 | 6 | 100 |

-continued

| Group Substance | Total Dose (mg/animal/4 d) | N | Fertility absol. | Inhibition rel. % |
|---|---|---|---|---|
| Control | 0 | 6 | 0 | 0 |

As a comparison, the abortive action of RU 486 (11beta-(4-dimethylaminophenyl)-17beta-hydroxy-17alpha-(prop-1-inyl)-4,9-estradien-3-one; Ep-A-0057115) was determined: it exhibits in the described test also at a total dose of 2 mg only relative fertility inhibition of 80%.

The testing on the estrogenic and gonadotropic action took place in the colpotropic test. In this case, no action was determined with the claimed compounds.

The compounds of general formula I according to the invention can be used in the form of pharmaceutical preparations. The production of the preparations takes place according to methods of galenicals known in the art by mixing with organic inert vehicles, which are suitable for enteral, percutaneous or parenteral application.

The dosage of the compounds according to the invention for said indications is between 1 and 1000 mg daily.

The compounds of general formula I are produced according to the invention by a compound of general formula II

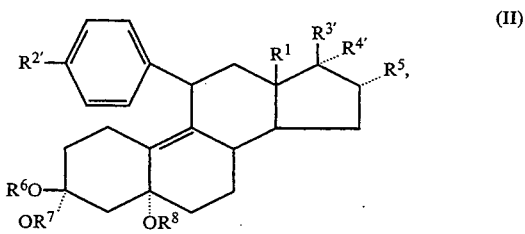

(II)

in which
R¹ and R⁵ have the meaning indicated in formula I,
R²', R³' and R⁴' have the same meaning as R² R³ and R⁴ in formula I,
and optionally existing keto and/or hydroxy groups can be protected,
R⁶ and R⁷ mean a methyl group or ethyl group each or together an ethylene or 2,2-dialkylpropylene group, especially a 2,2-dimethylpropylene group as well as
R⁸ means a hydrogen atom or an alkyl radical with 1 to 6 carbon atoms,
by acid treatment in a water-miscible solvent, optionally with heating to 60°–80° C., being converted into a compound of general formula I.

For example, aqueous acetic acid, p-toluenesulfonic acid or mineral acids such as hydrochloric acid, sulfuric acid, phosphoric acid or percholoric acid are used as acids for the acid treatment and aqueous methanol, ethanol or acetone is used as solvent. Optionally it is heated to 60° C. to 80° C. during the acid treatment.

The acid treatment can also be performed with an acid support, such as, e.g., an acid aluminum oxide.

The production of the starting products of general formula II to be used according to the invention takes place depending on the finally desired substituents according to different processes.

For synthesis of the starting products of general formula II, which ultimately result in the end products of general formula I with the substituents mentioned under A), the synthesis route reproduced in diagram I is used:

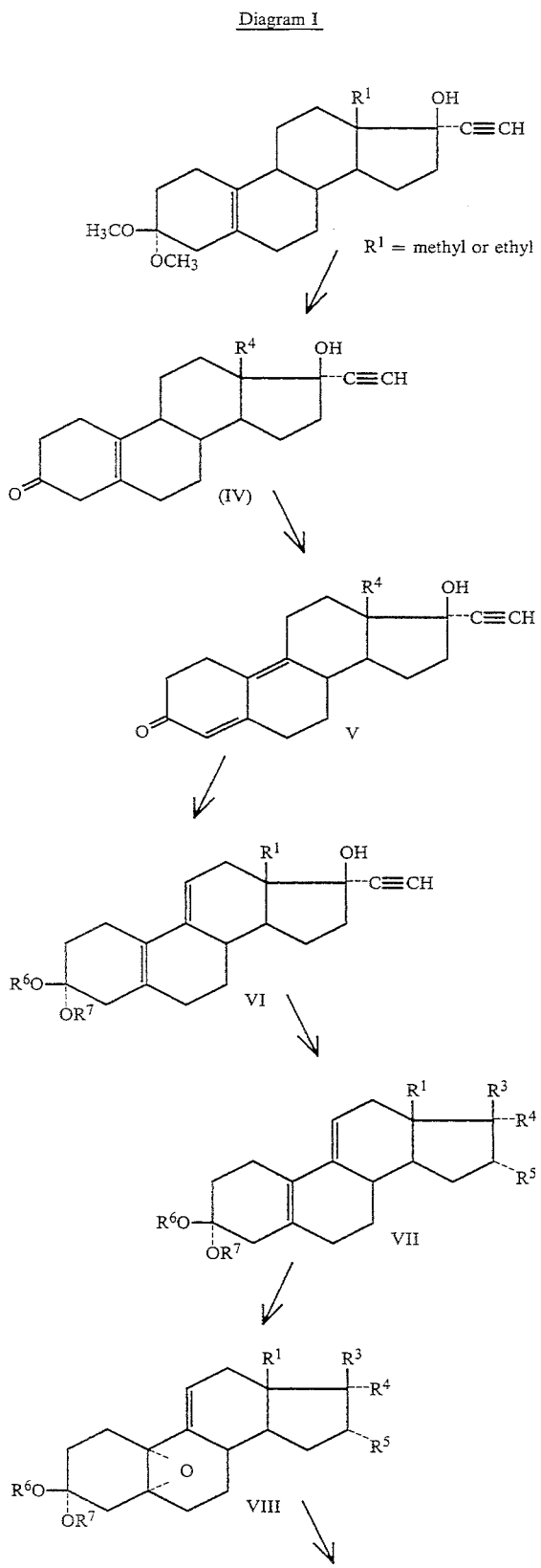

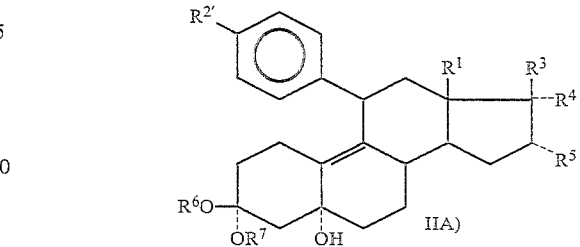

In this case
a) 3,3-dimethoxy-17alpha-ethinyl-gon-5(10)-en-17beta-ols of general formula III by ketal cleavage in an aqueous organic solvent in the presence of catalytic amounts of acid re-converted into 17alpha-ethinyl-gon-5(10)-en-3-ones of general formula IV,
b) 17alpha-ethinyl-gon-5(10)-en-3-ones IV are converted into 17alpha-ethinyl,17beta-hydroxy-gona-4,9-dien-3-ones of general formula V by bromation/dehydrobromation,
c) from 17alpha-ethinyl,17beta-hydroxy-gona-4,9-dien-3-ones V by ketalization there are produced the ketals of general formula VI, in which $R^7$ and $R^6 = CH_3$, $C_2H_5$ or a cyclic ketal with 2 or 3 C ring atoms, which can be substituted on the carbon atoms by alkyl groups, are represented,
d) ketals VI, by a base in an ether or an aprotic dipolar solvent, optionally with addition of a solubilizer, are converted into the acetylides and/or alcoholate, which optionally C- and/or O-alkylated with an alkylation agent or by hydroxymethylation of the ethinyl group with formaldehyde is converted into gona-(10),9(11)-dienes of general formula VII,
e) from gona-5(10),9(11)-dienes VII the 5alpha,10alpha-epoxides of general formula VIII are synthesized by epoxidizing and
f) 5alpha,10alpha-epoxides VIII are allowed to react with an aryl magnesium halide in the presence of a Cu(I) salt at a reaction temperature of $-30°$ C. to $+30°$ C. and the compounds are reduced with a 17alpha-propargyl group, and 11beta-aryl-5alpha-hydroxy-gon-9-enes of general formula II A result.

Preferably in process step a) acetone, methanol or a solvent combination, consisting of methylene chloride and tert-butanol, are used as organic solvents, and oxalic acid, p-toluenesulfonic acid or mineral acids such as sulfuric acid, hydrochloric acid, perchloric acid or phosphoric acid are used as acids.

in process step b)
pyridine hydrobromide perbromide or bromine in pyridine are used for the bromation/dehydrobromation in process step c)
for the ketalization there are used as alcohols methanol, ethanol, ethylene glycol or 2,3-dimethylpropanediol, as acids p-toluenesulfonic acid, oxalic acid, pyridinium rosylate or mineral acids, such as sulfuric acid or perchloric acid, as dehydrating agents formic acid triethyl ester and formic acid trimethyl ester or a water entrainer, such as chloroform, benzene or toluene, in process step d)

as bases there are used lithium alkyls such as lithium methyl, lithium-n-butyl and lithium-tert-butyl, sodium hydride, potassium hydroxide, lithium naphthalide, sodium naphthalide or potassium naphthalide, or naphthalide ion produced by electrochemical reduction, such as ethers, diethyl ether, tetrahydrofuran or dioxane, dimethyl sulfoxide, dimethyl formamide, as solubilizers optionally to be used benzene or toluene, add as alkylating agents dialkyl sulfates, such as dimethyl sulfate and diethyl sulfate, and alkyl halides such as methyl halide, ethyl halide, propyl halide, butyl halide, pentyl halide, hexyl halide, isopropyl halide in the form of the chlorides, bromides and iodides, as well as methyl chloroalkyl ether with an alkyl meaning n=1 to 6, in process step e)

as buffers there are used $Na_2CO_3$, $NaHCO_3$, $K_2CO_3$, $KHCO_3$, $Na_2HPO_4$, $NaH_2PO_4$, NaOAc and KOAc as well as inert solvents benzene, toluene, chloroform, dichloroethylene or methylene chloride and in process step f)

as aryl magnesium halides there are used phenyl magnesium halides in the form of chlorides and bromides, which in the opposition to the magnesium contain an $OCH_3$, $SCH_3$, $N(CH_3)_2$, $NHCH_3$, CN, $CH_3CHOH$, $R_4O$ $CH—OR_5$, $CH_3—COR_4—OR_5$ group, and $R_5=R_2=CH_3$, represents $C_2H_5$ or a cyclic ketal with 2 or 3 C ring atoms, which can be substituted on the carbon toms by alkyl groups, as ethers there can be used diethyl ether, tetrahydrofuran and dioxane, as solubilizers benzene and toluene, as Cu(I) salts CuCn, CuI and CuCl as well as reducing agents for the 17alphapropargyl group there can be used lithium alanate or hydrogen in he presence of pd or pt as hydrogenating catalyst in an ether or an alcohol.

In the especially preferred embodiment of the process the alkylation of the 17alpha-ethinyl function or of the 17beta-oxygen function or the hydroxymethylation of the 17alpha-ethinyl group is also performed starting from the educts according to formula I.

With the proposed process, starting from an industrially easily accessible starting product, compounds with different substitution on C atom 17 can be produced with relatively simple raw and auxiliary materials. In this way, besides the 17alpha-ethinyl ether, the 17alpha-propinyl ether, 17alpha-hydroxypropinyl ether and also at the same time the various 17beta-alkyl ethers become accessible.

To obtain the starting products of general formula necessary for the end products of general formula I with the substituents mentioned under B) a compound of general formula IIB, analogously to the compound of IIA from diagram 1,

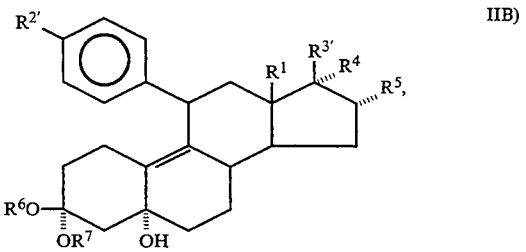

IIB)

in which $R^{2'}$ has the same meaning as $R^2$ in formula I under B), and an optionally present carbonyl group is protected as ketal, and $R^1$ $R^3$ $R^4$ and $R^5$ have the same meaning as in formula I) under B as well as $R^6$ and $R^7$ have the same meaning as in formula II) and $R^3$, moreover can be $OSi(CH_3)_3$, —OH, $CH_3CHOH$, $CH_2O$ alkanoyl and $CH_3CHO$ alkanoyl with 1 to 6 carbon atoms, by a base is converted into the corresponding alcoholates and the latter is then converted, by addition of an alkylating agent, into the corresponding ethers (i.e., into a compound of general formula II, in which $R^8$ is an alkyl radical).

(Starting products: DD-PS 277685, DD-PS 251142)

In this case, all hydroxy groups present in the compound of general formula IIB) are coalkylated.

Ethinyl groups are optionally coalkylated with acid hydrogen.

As bases there are used KOH, NaH, LiH, lithium alkyls such as lithium methyl, lithium n-butyl and lithium tert-butyl, calcium, lithium, sodium or potassium amides and lithium, sodium or potassium naphthalide and naphthalide ion produced by electrochemical reduction, are worked in an ether such as diethyl ether, tetrahydrofuran or dioxane, optionally with addition of a solubilizer such as benzene or toluene, and there are used as alkylating agents dialkyl sulfates such as dimethyl sulfate and diethyl sulfate, and alkyl halides such as methyl, ethyl, propyl, butyl, pentyl, hexyl, isopropyl halides in the form of the chlorides, bromides and iodides, as well as methylchloroalkyl ether with an alkyl radical meaning n=1-6.

Coalkylation of optionally present ethinyl groups is preferred.

To perform O and C alkylations at the same time, both the base amount and the amount of alkylating agent is to be matched to the number of the groups to be deprotonated.

With the proposed process it is possible, starting from 11beta-aryl-estr-9-en-5alpha-ols to perform selective alkylations on the steroid molecule and thus to provide an access to biologically active compounds. Here, the circumstance is used that 5alpha-Oalkyl ethers, which themselves are of pharmacological interest because of their structural features, surprisingly can easily be converted with cleavage of alcohol into 4,9-dien-9-ones.

It is to be emphasized that products obtained by alkylation of the 17-OH group and optionally the 17-ethinyl group have a great antigestagen effectiveness, as tests on rats show.

Starting products II, which for the production of the end compounds of general formula I with the substituents mentioned under C), are produced as indicated in the following diagram.

In this case,
a) 17alpha-alkoxymethyl-17beta-hydroxy-estra-5(10), 9(11)-diene-3-ketals XII are converted by deprotonation with bases into 17beta-alcoholates XIII of 17alpha-alkoxy-methyl-estra-5(10), 9(11)-diene-3-ketals,
b) the latter are reacted by alkylation with alkyl halides to 17beta-alkoxy-17alpha-alkoxy-methyl-estra-5(10), 9(11)-diene-3-ketals XIV,
c) the latter are selectively epoxidized with $H_2O_2$ to the 5alpha, 10alpha-epoxy-17beta-alkoxy-17alpha-alkoxyethyl-estr-9(11)-ene-3-ketals XV and
d) the latter with aryl magnesium halides, which: in the p-position to the magnesium have a dimethyl-amino or a protected acetyl group, are opened to the 11beta-aryl substituted 17beta- alkoxy-17alpha-alkoxymethyl-estr-9-en-5alpha-ols IIC).

Preferably the 3,3-dimethyl ketals are used as 17alpha-alkoxymethyl-17beta-hydroxy-estra-5(10), 9(11) diene ketals XII), alkali naphthalide is used as base for the deprotonation and tetrahydrofuran as organic solvent for formation of the alcoholates of general formula XIII. The alkylation is performed with alkyl halides, alkoxyalkyl halides or alkylthioalkyl halides directly or in solvents, and the 17beta-alkoxy-17alpha-alkoxymethyl-estra-5(10),9(11)-diene-3-ketals of general formula XIV result. The latter, by epoxidizing with $H_2O_2$ and haloacetones in he presence of catalytic amounts of tertiary bases or with haloaldehydes in the presence of hydrophilic agents in inert solvents, are converted into 5alpha, 10alpha-epoxy-17beta-alkoxy-17alpha-alkoxymethyl-est-9(11)-ene-3-ketals of general formula XV and by Grignardization in an ether in he presence of copper(I) salts is reacted with a p-bromo-(2'-methyl-1',3'-dioxolan-2'-yl)-benzene to the 11beta-aryl-substituted 17beta-alkoxy-17alpha-alkoxymethyl-estra-9-en5alpha-ols of general formula IIC).

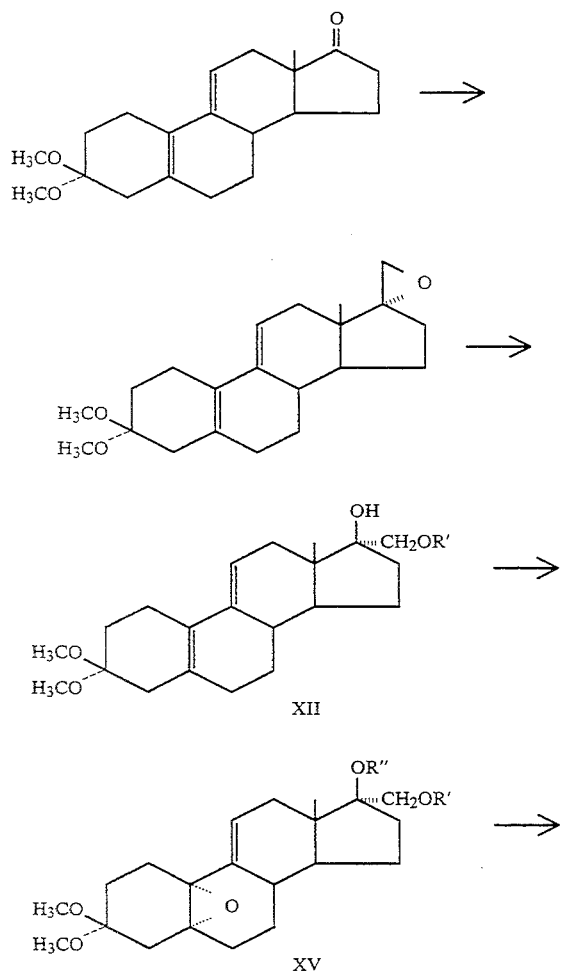

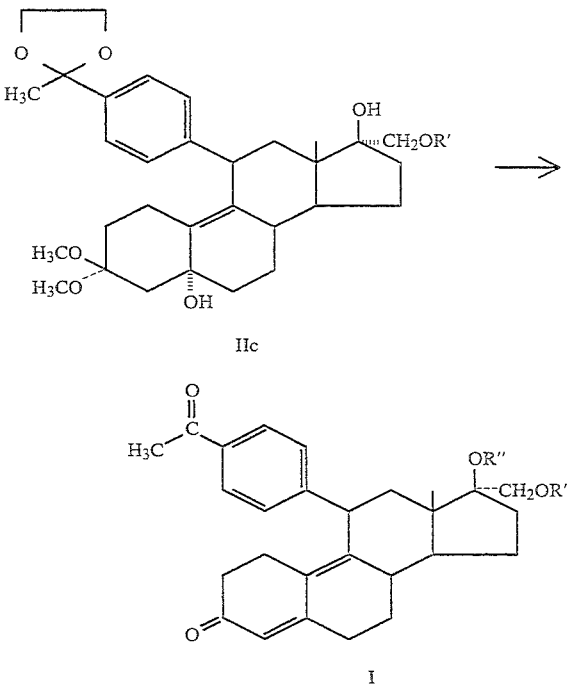

Especially 17alpha-alkoxymethyl-17beta-hydroxy-estra-5(10),9(11)-diene-3-dimethyl ketals of general formula XII are deprotonated with sodium naphthalide or lithium naphthalide in tetrahydrofuran and are reacted with alkyl halides, akyloxyalkyl halides, alkylthioalkyl halides directly or in ether at temperatures of 20° C. to the 17beta-alkoxy-17alpha-alkoxymethyl-estra-5(10)9(11)-diene-3-ketals of general formula XIV. The epoxidation with $H_2O_2$ and hexachloroacetone or hexafluoroacetone takes place in the presence of catalytic amounts of triethylamine or pyridine, or else with chloral hydrate in the presence of anhydrous primary alkali phosphate and alkali bicarbonate or alkali carbonate at temperatures around 20° C. in methylene chloride or chloroform, and the 5alpha,10alpha-epoxy-17beta-alkoxy-17alpha-alkoxymethyl-estr-9(11)-ene-3-ketals of general formula XV result. By Grignardization in tetrahydrofuran with CuCl and p-bromo(2'-methyl-1',3'-dioxolan-2'-yl)-benzene at temperatures between 0° C. and 30° C. the 11beta-aryl-substituted 17beta-alkoxy-17alpha-alkoxymethyl-estr-9-en-5alpha-ols of general formula II are formed.

The following examples provide for a more detailed explanation of the invention.

EXAMPLE 1

17alpha-Ethinyl-17beta-hydroxy-13-methyl-gon-5(10)-en-3-one 10 g of 3,3-dimethoxy-17alpha-ethinyl-13-methyl-gon-5(10)en-17beta-ol is suspended in 165 ml of 80% aqueous acetone and mixed with 0.2 ml of 25% sulfuric acid with vigorous stirring. Then it is stirred at room temperature until all the starting material is reacted. Then the steroid is precipitated by addition of water, separated and dried. 9 g of the 3-keto-5(10)-ene compound is obtained, which can be recrystallized from acetone/water.

Mp: crude product: 173° C. to 174° C.

b) 17alpha-Ethinyl-17beta-hydroxy-13-methyl-gona-4,9-dien-3-one 15 g of 17alpha-ethinyl-17beta-hydroxy-13-methyl-gon-5(10)-en-3-one is dissolved in 219 ml of pyridine and mixed all at once with 18.6 g of pyridine hydrobromide perbromide with cooling (−5° C.). After 15 minutes, the cooling is removed and the solution slowly warming to room temperature is stirred for about 15 more minutes and then 2 ml of methyl butene is added to decompose the excess bromation agent. Then it is stirred for 5 hours at room temperature and the stirred into ice water to which some hydrochloric acid has been previously added. After crystallization, the steroid is suctioned off and optionally crystallized from ether. 14 g of tile dienone (92.7% of theory) is obtained.

Mp: crude product: 168° C. to 173° C.

c) 17alpha-Ethinyl-3,3-ethylenedioxy-13-methyl-gona-5(10),9(11)-dien-17beta-ol 2 g of 17alpha-ethinyl-17beta-hydroxy-13-methyl-gona-4,9-dien-3-one is dissolved in 3 ml of ethylene glycol, 5 ml of orthoformic acid triethyl ester and 30 ml of methylene chloride and mixed with 0.1 g of p-toluenesulfonic acid. Some solvent is distilled off and a dark brown solution is obtained, which is stirred for 30 minutes at room temperature. Then it is mixed with an aqueous sodium bicarbonate solution and the steroid is extracted with methylene chloride. After concentration of the extracts by evaporation, an oil residue is crystallized from ether/hexane and 2 g of the ketal is obtained.

Mp: 152° C. to 155° C.
IR[cm$^{-1}$]: no C=O, 3300 (ethinyl), 3600 (OH)

c') 17alpha-Ethinyl-3,3-ethylenedioxy-13-methyl-gona-5(10),9(11)-dien-17beta-ol 42.5 g of 17alpha-ethinyl-17beta-hydroxy-13-methyl-gona-4,9-dien-3-one (crude product) is dissolved in 600 ml of benzene and mixed with 45 ml of ethylene glycol and 1.8 g of p-toluenesulfonic acid and boiled on the water separator with intensive stirring until (about 2 hours) all the starting material is reacted. Then a sodium bicarbonate solution is added and the steroid is extracted with benzene. The oily residue obtainable after concentration by evaporation is crystallized from ether, and 43 g of ketal is obtained.

Mp: 152° C. to 155° C.
IR[cm$^{-1}$]: no C=O, 3300 (ethinyl), 3600 (OH)

d) 3,3-Ethylenedioxy-17alpha-ethinyl-17beta-methoxy13-methyl-gona-5(10 ), 9(11 )-diene 7.5 g of 3,3-ethylenedioxy-17alpha-ethinyl-13-methyl-gona-5(10),9(11)-dien-17beta-ol (22.07 mmol of crude product) is dissolved in 25 ml of tetrahydrofuran and mixed cold (-10° C.) under inert gas with 55 ml (22 mmol, 0.4 m) of an ethereal lithium methyl solution. In the addition a strong formation of gas begins. After the completed addition, 5.7 ml of methyl iodide is added after 15 minutes and the reaction solution is heated to room temperature. It is allowed to stand overnight at room temperature, then mixed with water and the steroid is extracted with ether. After concentration of the extracts by evaporation, it is chromatographed on neutral aluminum oxide. A benzene/benzene-ethyl acetate mixture (5: 1 ) is used as eluant. 4.3 g of the 17beta methyl ether is isolated in the form of an oil, which can be used directly in the next step.

IR[cm$^{-1}$]: no C=O, 3300 (ethinyl)

d') 3,3-Ethylenedioxy-17alpha-ethinyl-17beta-methoxy-13-methyl-gona-5(10), 9(11 )-diene 7 g of 3,3-ethylenedioxy-17alpha-ethinyl-13-methyl-gona-5(10),9(11)-dien-17beta-ol (20.6 mmol) is dissolved in 50 ml of tetrahydrofuran and mixed under nitrogen with 1 g of naphthalene (7.8 mmol) and 0.2 g of lithium (28.57 mmol) and stirred for 5 hours at about 70° C. (hot plate temperature). Then the unconsumed lithium is removed and 2.6 ml (41.72 mmol) of methyl iodide is added to the solution at room temperature. Then it is gently heated on the water bath for about 4 hours and the steroid is extracted with ether after addition of water. The crude product obtainable after concentration of the extracts by evaporation is used in the next step without further purification.

IR[cm$^{-1}$]: no C=O, 3300 ( ethinyl )

e) 17alpha-ethinyl-3,3-ethylenedioxy-17beta-methoxy-5alpha, 10alpha-epoxy-13-methyl-gon-9-ene 5 g of 17alpha-ethinyl-3,3-ethylenedioxy-17beta-methoxy-13-methyl-gona-5(10),9(11)-diene is dissolved in 45 ml of methylene chloride and after addition of 2 g of Na$_2$HPO$_4$, 1 g of Na$_2$CO$_3$ and 7.25 ml of 30% H$_2$O$_2$ is stirred intensively and then mixed with 1.25 g (7.55 mmol) of chloral hydrate. It is stirred for about 20 hours at room temperature and then an aqueous sodium carbonate solution is added and the steroid is extracted with methylene chloride. The organic phase is repeatedly washed with sodium carbonate solution, then separated, dried and concentrated by evaporation. The remaining residue is flash chromatographed on the basic aluminum oxide with benzene/ethyl acetate (20:1 to 10:1). The epoxide is isolated in the form of an oil (2 g) and thus is used in the next step.

IR[cm$^{-1}$]: no C=O f) 17alpha-Ethinyl-3,3-ethylenedioxy-11beta-[4-(2'-methyl-1',3'-dioxolan-2'-yl)-phenyl]-17beta-methoxy-13-methyl-gon-9-en-5alpha-ol About 1.5 g of 17alpha-ethinyl-3,3-ethylenedioxy-17beta-methoxy-5alpha,10alpha-epoxy-13-methyl-gon-9(11)-ene (4.05 mmol) in 10 ml of tetrahydrofuran is instilled in a freshly prepared Grignard solution, cooled to −15° C., of 4-(2'-methyl-1',3'-dioxolan-2'-yl)-phenyl magnesium bromide (15 mmol) and 0.15 g of CuCl in 30 ml of tetrahydrofuran. After the addition is completed, it is stirred for about 30 minutes and in doing so the reaction mixture is gradually heated to room temperature. Then it is mixed with an aqueous ammonium chloride solution and the steroid is extracted with ether. After concentration of the extracts by evaporation, the remaining residue is flash chromatographed on basic aluminum oxide with benzene/ethyl acetate (10:1). 1.2 g of the 11beta-aryl substituted compound is isolated, which can be crystallized from methanol or ethanol.

Mp: 181° C. to 189° C. ]α]$_D$: 31.1° g)
11beta-(4-Acetylphenyl)-17alpha-ethinyl-17beta-methoxy-13-methyl-gona-4,9-dien-3-one 0.5 g of 17alpha-ethinyl-3,3-ethylenedioxy-11beta-[4-(2'methyl-1', 3'-dioxolan-2'-yl)-phenyl]-17beta-methoxy-13-methyl-gon-9-en-5alpha-ol (0.94 mmol) is mixed with 10 ml of 70% aqueous acetic acid and heated for 1 hour at 70° C. on the water bath. Then the steroid is precipitated by addition of water and some ammonia. The isolated crude product is flash chromatographed on neutral aluminum oxide. The elution takes place with benzene/ethyl acetate mixture (10:1). 0.35 g of the 11beta-acetophenyl compound precipitating in amorphous crystalline form from methanol/water is obtained.

Mp: 87° C. to 91° C. $[\alpha]_D$: 139.3°

EXAMPLE 2

The production of steps a to e takes place analogously to example 1.

f)
11beta-(4-dimethylaminophenyl)-3,3-ethylenedioxy-17alpha-propinyl-13-methyl-gon-9-ene-5alpha,17beta-diol A Grignard solution in tetrahydrofuran, prepared from 1.92 g of magnesium, 0.05 ml of dibromoethane, 16.8 g of pbromodimethylaminobenzene (80 mmol) and 120 ml of tetrahydrofuran, is cooled with dry ice to about −15° C. and mixed with 0.4 g of CuCl. After 15 minutes stirring, about 9 g of 3,3-ethylenedioxy-5alpha,10alpha-epoxy-17alpha-propinyl-13-methyl-gon-9(11)-en-17beta-ol (crude product), which is dissolved in 15 ml of tetrahydrofuran, is instilled cold. Then it is stirred for 30 minutes more and the solution is slowly allowed to warm to room temperature. After working up, it is mixed with aqueous ammonium chloride solution and the steroid is extracted with ether. The organic phase is washed with an aqueous sodium disulfite solution and finally with water, dried and concentrated by evaporation. The remaining residue is chromatographed on basic aluminum oxide. The elution takes place with benzene/benzene-ethyl acetate mixture (10: 1 ). After recrystallization from ether/n-hexane, 5.1 g of the dimethylaminophenyl compound is obtained.

Mp: 203° C. to 206° C.
IR[cm$^{-1}$]: 3600 (OH), 3500 (OH-associated)

f') 11beta-(4-dimethylaminophenyl)-3,3-ethylenedioxy-17beta-methoxy-17alpha-propinyl-13-methyl-gon-9-en-5alpha-ol 40 ml of a Grignard solution 30 (mmol) in tetrahydrofuran, prepared from 0.96 g of magnesium, 0.05 ml of debromoethane, 8.4 g of p-bromodimethylaminobenzene in 60 ml of tetrahydrofuran, is cooled with dry ice to −15° C. and mixed with 0.2 g of CuCl. After 15 minutes stirring under nitrogen 2.1 g of 3,3-ethylenedioxy17beta-methoxy-5alpha, 10alpha-epoxy-17alpha-propinyl-13-methyl-gon-9(11 )-ene, which is dissolved in 10 ml of tetrahydrofuran, is instilled cold. Then the external cooling is removed and it is stirred for 30 more minutes. For working up it is mixed with aqueous ammonium chloride and the steroid is extracted with ether. Then it is washed with aqueous sodium disulfite solution and finally with water, the organic phase is separated, dried and concentrated by evaporation. The remaining residue is chromatographed on basic aluminum oxide. Benzene and benzene/ethyl acetate mixture (10:1) is used as mobile phase. After recrystallization from ether/n-hexane, 1.5 g of the 11beta-dimethylaminophenyl compound is obtained.

Mp: 124° C. to 127° C. $[\alpha]_D$: −69.9° g)
11beta-(4-dimethylaminophenyl)-17beta-hydroxy-17alpha-propinyl-13-methyl-gona-4,9-dien-3-one 2.9 of 11beta-(4-dimethylaminophenyl)-3,3-ethylenedioxy-17alpha-propinyl-13-methyl-gon-9-en-5alpha,17beta-diol is dissolved in 10 ml of 70% aqueous acetic acid and heated for one hour on the water bath (60° C. to 70° C.). Then the steroid is precipitated by addition of water and 25% ammonia. The precipitating crude product (about 2.5 g) is chromatographed on basic aluminum oxide with benzene and benzene/ethyl acetate (10:1). After recrystallization from acetonitrile 1.3 g of the dienone is obtained.

Mp: 178° C. to 181° C.

g')
11beta-(4-dimethylaminophenyl)-17beta-methoxy-17alpha-propinyl-13-methyl-gona-4,9-dien-3-one 0.7 g of 11beta-(4-dimethylaminophenyl-3,3-ethylenedioxy-17beta-methoxy-17alpha-propinyl-13-methyl-gon-9-en-5alpha-ol is dissolved in 10 ml of 70% aqueous acetic acid and is heated for 1 hour on the water bath (60° C. to 70° C.). Following this, the steroid is precipitated by addition of water and 25% ammonia. The easily frittable crude product is flash chromatographed on basic aluminum oxide with benzene and benzene/ethyl acetate (10:1). The residue obtainable after concentration of the dienone fraction by evaporation is dissolved in acetic acid and the steroid is precipitated by addition of water and 25% ammonia. 0.35% b of the 11beta-dimethylaminophenyl dienone is obtained.

Mp: 101° C. to 105° C. $[\alpha]_D$: 129.5° C.

EXAMPLE 3

The production of steps a' to c takes place analogously to example 1.

d)
3,3-Ethylenedioxy-17alpha-propinyl-13-methyl-gona-5(10),9(11)-dien-17beta-ol 9 g of 17alpha-ethinyl-3,3-ethylenedioxy-13-methyl-gona-5(10),9(11)-dien-17beta-ol (26.4 mmol) is dissolved in 70 ml of tetrahydrofuran and mixed with 86.5 ml of lithium butyl (0.61 m) with cooling (about -10° C.). 4 ml of methylene iodide (109.6 mmol), which is diluted with 4 ml of tetrahydrofuran, is gradually added cold to the homogeneous solution and is slowly allowed to heat to room temperature with stirring. After 4 hours it is mixed with water and the steroid is extracted with ether. The oily residue (9 g of crude product) obtainable after concentration by evaporation can be crystallized from hexane.

IR[cm$^{-1}$]: no C=O, 3595 (OH)

e) 3,3-Ethylenedioxy-5alpha, 10alpha-epoxy-17alpha-propinyl-13-methyl-gon-9(11 )-en-17beta-ol 9 g of 3,3-ethylenedioxy-17alpha-propinyl-13-methyl-gona-5(10) ,9(11)-dien-17beta-ol (crude product), 3 g of anhydrous Na$_2$HPO$_4$ and 2 g of Na$_2$CO$_3$ are suspended in 45 ml of methylene chloride and mixed with 13.25 ml of H$_2$O$_2$ (30%) and finally with 2.25 g of chloral hydrate at room temperature with stirring. It is stirred at room temperature for 16 hours, then an aqueous sodium carbonate solution is added and the steroid is extracted with methylene chloride. The organic phase is washed twice more with a sodium carbonate solution and finally with water, then dried and concentrated by evaporation. The precipitating epoxide crude product is used in the next step without further purification.

IR[cm$^{-1}$]: no C=O, 3600 (OH)

EXAMPLE 4

The production of steps a to c takes place analogously to example 3.

d) 3,3-Ethylenedioxy-17beta-methoxy-17alpha-propinyl-13-methyl-gona-5(10 ), 9(11 )-diene 5 g of 3,3-ethylenedioxy-17alpha-ethinyl-13-methyl-gona-5(10),9(11)-dien-17beta-ol is dissolved in 40 ml of tetrahydrofuran and slowly mixed with 48 ml (0.61 m) of lithium butyl with cooling (−15° C.). 4.4 ml of methyl iodide, which is diluted with 4.4 ml of tetrahydrofuran, is slowly added cold to the homogeneous solution and then the solution is heated to room temperature with stirring. After 16 hours of reaction time, it is mixed with water and the steroid is extracted with ether. The residue obtainable after concentration of the ether extracts by evaporation can be used in the next step without purification. 5 g of the 17beta-methoxy-17alpha-propinyl compound is obtained.

IR[cm$^{-1}$]: no C=O, no OH
MS: M+ 368, calc. f. $C_{24}H_{32}O_3$ e) 3,3-Ethylenedioxy-17beta-methoxy-5alpha, 10alpha-epoxy-17alpha-propinyl-13-methyl-gon-9(11)-ene 5 g of 3,3-ethylenedioxy-17beta-methoxy-17alpha-propinyl-13-methyl-gona-5(10),9(11)-diene, 3 g of anhydrous $Na_2HPO_4$ and 2 g of $Na_2CO_3$ are suspended in 25 ml of methylene chloride and mixed with 8 ml of $H_2O_2$ (30%) and finally with 1.5 g of chloral hydrate at room temperature with stirring. After tile reaction is complete, an aqueous sodium carbonate solution is added and the steroid is extracted with methylene chloride. The organic phase is washed twice more with a sodium carbonate solution and finally with water, then dried and concentrated by evaporation. The precipitating crude product is flash chromatographed on basic aluminum oxide with toluene/toluene-ethyl acetate mixture (10:1). 2.1 g of epoxide is isolated in the form of an oil, which is used directly in the next step.

IR[cm$^{-1}$]: no C=O f) 3,3-Ethylenedioxy-17beta-methoxy-11beta-[4-(2'-methyl-1',3'-dioxolan-2'-yl )-phenyl]-17alpha-propinyl-13-methyl-gon-9-en-5alpha-ol 0.05 ml of dibromoethane is added to a suspension of 0.72 g of magnesium shavings (30 mmol) in 5 ml of tetrahydrofuran and gradually 55 ml of tetrahydrofuran solution containing 7.35 g of p-bromo(2'-methyl-1',3'-dioxolan-2'-yl)-benzene (30 mmol) is added under argon so that the internal temperature does not exceed 45° C. In the starting phase, it is slightly heated (45° C.) and then the temperature is regulated by addition of aryl halide. After addition of the aryl halide is completed, it is stirred for 2 more hours at 45° C. 30 ml is taken from the Grignard solution thus prepared and mixed with 0.15 g of CuCl with cooling (−5° C. to −15° C.). It is stirred for 15 minutes with this temperature being maintained and then a solution of about 1 g of 3,3-ethylenedioxy-17beta-methoxy-5alpha, 10alpha-epoxy-17alpha-propinyl-13-methyl-gon-9(11)-ene in 10 ml of tetrahydrofuran is added cold. Then it is stirred for 1 hour under exclusion of moisture and nitrogen and the solution is gradually heated to room temperature. After the reaction is completed, it is mixed with aqueous ammonium chloride solution and the steroid is extracted with ether. After concentration of the extracts by evaporation, the remaining residue is flash chromatographed on basic aluminum oxide with benzene/ethyl acetate (10:1). 1.05 g of the target product is obtained in the form of an amorphous powder by precipitation with water from methanol solution.

IR[cm$^{-1}$]: 1600 (aromatic), 3500 (OH-associated)

g) 11beta-(4-Acetylphenyl)-17beta-methoxy-17alpha-propinyl-13-methyl-gona-4,9-dien-3-one 0.15 g of 3,3-ethylenedioxy-11beta-[4-(2'-methyl-1',3'-dioxolan-2'-yl)-phenyl]-17beta-methoxy-17alpha-propinyl-13-methyl-gon-9-en-5alpha-ol is dissolved in 10 ml of 70% aqueous acetic acid and heated on the water bath (60° C. to 70° C.) for about 1 hour. Then the solution is mixed cold with water and some ammonia, and steroid is precipitated in amorphous crystalline form. After chromatography of the steroid on neutral aluminum oxide with benzene/ethyl acetate (10:1), 0.09 g of the 4,9-dien-3-one is isolated, which can be crystallized from acetonitrile or ether.

Mp: 110° C. to 113° C. [α]$_D$: 102.3°

EXAMPLE 5

The production of steps a to c takes place analogously to example 1.

d) 3,3-Ethylenedioxy-17alpha-(3'-hydroxy-1'-propinyl)-17beta-methoxy-13-methyl-gona-5(10), 9(11 )-diene 4.3 g of 3,3-ethylenedioxy-17alpha-ethinyl-17beta-methoxy-13-methyl-gona-5(10),9(11)-diene is dissolved in 10 ml of tetrahydrofuran and mixed with 37.5 ml of freshly prepared lithium methyl solution (15 nmol, 0.4 m). Then 1 g of paraformaldehyde is added at room temperature. The reaction begins immediately. After the reaction is completed, water is added and the steroid is extracted with ether. After concentration by evaporation, about 4.4 g of crude product of the hydroxymethylated compound is obtained, which is used without purification in the next step.

IR[cm$^{-1}$]: no C=O, 3600 (OH)

e) 3,3-Ethylenedioxy-17alpha-(3'-hydroxy-1'-propinyl)-17beta-methoxy-5alpha,10alpha-epoxy-13-methyl-gon-9(11)-ene About 4.4 g of 3,3-ethylenedioxy-17alpha-(3'-hydroxy-1'-propinyl)-17beta-methoxy-13-methyl-gona-5(10),9(11)-diene is dissolved in 45 ml of methylene chloride and after addition of 2 g of $Na_2HPO_4$, 1 g of $Na_2CO_3$ and 7.25 ml of $H_2O_2$ (30%) are intensively stirred and then mixed with 1.25 g of chloral hydrate (7.55 mmol). It is stirred for 5 hours at room temperature and kept for 2.5 days in the refrigerator. Then an aqueous sodium carbonate solution is added and the steroid is extracted with methylene chloride. The organic phase is repeatedly washed with a sodium carbonate solution, then separated, dried and concentrated by evaporation. The remaining residue is flash chromatographed on basic aluminum oxide with benzene/ethyl acetate (4:1 to 2:1). 3.5 g of epoxide is isolated in the form of an oil, which is used directly in the next step.

IR[cm$^{-1}$]: no C=O, 3600 (OH)

f) 3,3-ethylenedioxy-17alpha-(3'-hydroxy-1'-propinyl)-17beta-methoxy-11beta-[4-(2'-methyl-1',3'-dioxolan-2-yl)-phenyl]-13-methyl-gon-9-en-5alpha-ol 1 g of 3,3-ethylenedioxy-17alpha-(3'-hydroxy-1'-propinyl)-17beta-methoxy-5alpha,10alpha-epoxy-13-methyl-gon-9(11)-ene (2.5 mmol) in 10 ml of tetrahydrofuran is instilled in a freshly prepared Grignard solution, cooled to −15° C., of 4-(2'-methyl--1',3'-dioxolan-2'-yl)-phenyl magnesium bromide (15 mmol) and 0.15 g of CuCl in 30 ml of tetrahydrofuran. After the addition is completed, it is stirred for about 30 minutes and the reaction mixture is slowly heated to room temperature. After the reaction is completed, it is mixed with an aqueous ammonium chloride solution and the steroid is extracted with ether. After concentration of the extracts by evaporation, the remaining residue is flash chromatographed on basic aluminum oxide. A benzene/ethyl acetate mixture (4:1 to 1:1) is used as mobile phase. 0.5 g of the 11beta-aryl substituted compound is isolated in the form of an oil, which is used directly in the next step.

IR[cm$^{-1}$]: 3600 (OH), 3500 (OH associated)

g) 11beta-(4-Acetylphenyl)-17alpha-(3'-hydroxy-1'(Z)-propenyl)-17beta-methoxy-13-methyl-gona-4,9-dien-3-one About 0.5 g of 3,3-ethylenedioxy-17alpha-(3'-hydroxy-1'(Z)-propenyl)-17beta-methoxy-11beta-[4-(2'-methyl-1',3'-dioxolan-2'-yl)-phenyl]-13-methyl-gon-9-en-5alpha-ol (1.09 mmol) is mixed with 10 ml of 70% aqueous acetic acid and heated for about 1 hour at 70° C. on the water bath. Then it is mixed with water and some ammonia and the product separating in an oily manner is extracted with methylene chloride. The residue remaining after concentration of the extracts by evaporation is flash chromatographed on neutral aluminum oxide with benzene/ethyl acetate (2:1). 0.25 g of the 11beta-acetophenyl compound crystallizing from methanol is obtained.

Mp: 118° C. to 124° C. [α]$_D$: 188.2° f) 3,3-Ethylenedioxy-17alpha-(3-hydroxy-1'(Z)-propenyl)-17beta-methoxy-11beta-[4-(2'-methyl-1',3'-dioxolan-2'-yl)-phenyl]-13-methyl-gon-9-en-5alpha-ol About 0.5 g of 3,3-ethylenedioxy-17alpha-(3'-hydroxy-1'-propinyl)-17beta-methoxy-11beta-[4-(2'-methyl-1',3'-dioxolan-2'-yl)-phenyl]-13-methyl-gon-9-en-5alpha-ol is dissolved in 8 ml of tetrahydrofuran and 8.75 ml of pyridine and, after addition of 0.1 g of Pd/BaSO$_4$ (10%) at room temperature is hydrogenated in a hydrogen atmosphere under standard pressure until standstill of the hydrogen absorption. After a few minutes, the oxide catalyst, at first colored brown, is reduced (black coloring). After one hour the hydrogen absorption is finished. It is filtered from the catalyst and the filtrate evaporated to dryness is used directly in the next step.

IR[cm$^{-1}$]: 3600 (OH), 3500 (OH-associated)

EXAMPLE 6 a) 16alpha, 17alpha—Cyclohexano-3,3-ethylenedioxy-17beta-methoxymethyl-5alpha-methoxy-11beta-[4-2'methyl-1', 3'-dioxolan-2'-yl )-phenyl]-estr-9-ene 0.1 g of 16alpha, 17alpha-cyclohexano-3,3-ethylenedioxy-17beta-hydroxymethyl-11beta-[4-2'methyl-1', 3'-dioxolan-2'-yl ) phenyl]-estr-9-en-5alpha-ol is dissolved in 5 ml of absolute benzene and 0.5 ml methyl iodide and, after addition of 0.4 g of pulverized KOH, is stirred at 35° C. for about 48 hours with exclusion of moisture. After quantitative reaction has been completed, it is mixed with water and the steroid is extracted with benzene. 8.1 g of the dimethylated compound is obtained in the form of an oil.

IR[cm$^{-1}$]: 1600 (aromatic)

1H-NMR[ppm]: 7.33; 7.23; 7.18; 7.09 (4H, aromatic); 4.18 and 4.12 (1H, 11alpha-H), 3.89 (8H, ketal), 3.22 (6H, 2x OMe), 1.61 (3H, acetophenyl ketal), 0.39 (3H, 13 Me)

b) 11beta-(4-Acetylphenyl)-16alpha,17alpha-cyclohexano-17beta-methoxymethyl-estra-4,9-dien-3-one 0.1 g of 16alpha,17alpha-cyclohexano-3,3-ethylenedioxy-17beta-methoxymethyl-5alpha-methoxy-11beta-[4-(2'methyl-1',3'-dioxolan-2'-yl)-phenyl]-estr-9-ene is dissolved in 5 ml of 70% aqueous acetic acid and stirred on the water bath at 60° C. for about 1 hour. After the reaction is complete, it is mixed with water and the amorphous crystalline crude product is chromatographed on basic aluminum oxide with benzene/ethyl acetate (20:1). After concentration of the eluates by evaporation, the remaining residue is precipitated from acetic acid by addition of water.

IR[cm$^{-1}$]: 1600 (aromatic); 1660 (3 ketal); 1685 (C=O acetyl)

MS: M$^+$ 472 calc. f. C$_{32}$H$_{40}$O$_3$: M$^+$ −40 calc. f. C$_{31}$H$_{36}$O$_2$

EXAMPLE 7

11beta- (4-acetylphenyl )-17beta-methoxy-17alpha-methoxymethyl-estra-4,9-dien-3-one a) 2.6 g of 3,3-dimethoxy-17alpha-methoxymethyl-estra-5(10),9(11)-dien-17beta-ol is dissolved in 20 ml THF and instilled in a solution of sodium naphthalide (produced from 1.28 g of naphthalene and 250 mg of sodium in 50 ml of THF) at 20° C., and the alcoholate is formed.

b) 5 ml of methyl iodide is added to the dark green solution after 30 minutes at 20° C. and it is stirred for 2 hours at this temperature, decomposed with methanol and then with water, extracted with ethyl acetate, the organic phase is washed neutral, dried on K$_2$CO$_3$ and Na$_2$SO$_4$ and the solvent is evaporated under vacuum. The crude product (6.7 g) is purified by column chromatography on 120 g of aluminum oxide (alkaline) with a benzene/ethyl acetate gradient. 2.36 g of 17beta-methoxy17alpha-methoxymethyl-estra-5(10),9(11 )-diene-3,3-dimethyl ketal is obtained as colorless oil.

[α]$_D$: +110° (CHCl$_3$, c=0.45)

c) 1.88 g of 17beta-methoxy-17alpha-methoxymethyl-estra5(10),9(11)-diene-3,3-dimethyl ketal is dissolved in a mixture of 15 ml of methylene chloride and 0.5 ml pyridine and is mixed with 2 ml H$_2$O$_2$ and 0.2 ml hexachloroacetone at 20° C. After 20 hours aqueous bisulfite solution is added and it is extracted with methylene chloride. It is washed neutral, dried on K$_2$CO$_3$ and Na$_2$SO$_4$ and the solvent is distilled off under vacuum. The crude product is purified by column chromatography on 70 g of aluminum oxide (alkaline) with a benzene/ethyl acetate gradient. 1.24 g of 5alpha,10alpha-epoxy-17beta-methoxy-17alpha-methoxymethyl-estr-9(11)-ene-3,3-dimethyl ketal is obtained.

Mp: 116° C. to 119° C. (hexane)

$[\alpha]_D$: +7° C. (CHCl$_3$)

d) 0.15 ml of dibromoethane and then 4.95 g of 1-(4-bromophenyl)-ethanon-1,1-ethylene ketal in 30 ml of abs. THF are instilled in 486 mg of magnesium in 5 ml of abs. ether under argon. It is stirred for 3 hours at 50° C. internal temperature, cooled to 0° C. and 170 mg of CuCl is added. After another 20 minutes, 1.18 g of 5alpha, 10alpha-epoxy-17beta-methoxy-17alpha-methoxymethyl-estr-9(11)-ene-3,3-dimethyl ketal in 20 ml of THF is instilled. It is stirred for 2 hours at room temperature, the batch is decomposed with aqueous ammonium chloride solution and extracted with ethyl acetate. The organic phase is washed neutral, dried on Na$_2$SO$_4$ and evaporated under vacuum. The crude product is purified by column chromatography on 70 g of aluminum oxide (alkaline) with a benzene/ethyl acetate gradient. 970 mg of 3,3-dimethoxy-11beta-[4-(1,1-ethylenedioxyethyl)-phenyl]-17beta-methoxy-17alpha-methoxymethyl-estr-9-en-5alpha-ol is obtained as colorless oil, which is further directly processed.

e) 970 mg of 3,3-dimethoxy-11beta-[4-(1,1-ethylenedioxyethyl)-phenyl]-17beta-methoxy-17alpha-methoxymethyl-estr-9-en-5alpha-ol is stirred in 20 ml of dilute acetic acid for 20 hours at room temperature. After addition of water, it is extracted with ethyl acetate, the organic phase is washed with dilute aqueous NaOH and water, dried on Na$_2$SO$_4$ and evaporated under vacuum. After recrystallization from ether, 430 mg of 11beta-(4-acetylphenyl)-17beta-methoxy-17alpha-methoxymethyl-estra-4,9-dien-3-one is obtained.

Mp: 133° C. to 137° C. (ether)

$[\alpha]_D$: +170° (CHCl$_3$)

EXAMPLE 8

11beta-(4-Acetylphenyl)-17alpha-ethoxymethyl-17beta-methoxy-estra-4,9-dien-3-one a) A sodium naphthalide solution (produced from 250 mg of sodium and 1.28 g of naphthalene in 50 ml of THF) is instilled in 1.88 g of 3,3-dimethoxy-17alpha-ethoxymethyl-estra-5(10),9(11)-dien-17beta-ol in 30 ml of THF until a dark green coloring remains, and the alcoholate is formed.

b) After 30 minutes at room temperature 4 ml of methyl iodide is added and stirred for 2 more hours. The batch is decomposed with aqueous NH$_4$Cl solution, extracted with ethyl acetate. The organic phase is washed neutral, dried on K$_2$CO$_3$ and Na$_2$SO$_4$ and the solvent is evaporated under vacuum. The crude product is purified by column chromatography on aluminum oxide (alkaline) with a benzene/ethyl acetate gradient. 1.56 g of 17alpha-ethoxymethyl-17beta-methoxy-estra-5(10),9(11)-diene-3,3dimethyl ketal is obtained as colorless oil, which is used directly in the next step.

c) 1.56 g of 17alpha-ethoxymethyl-17beta-methoxy-estra-5(10),9(11)-diene-3,3-dimethyl ketal is dissolved in 20 ml of methylene chloride and 0.5 ml of pyridine and mixed with 3 ml of H$_2$O$_2$ and 0.3 ml of hexachloroacetone at 20° C. After 20 hours aqueous bisulfite solution is added and extracted with methylene chloride. It is washed neutral, dried on K$_2$CO$_3$ and Na$_2$SO$_4$ and the solvent is distilled off under vacuum. The crude product is purified by column chromatography on 60 g of aluminum oxide (alkaline) with a benzene/ethyl acetate gradient. 940 mg of 5alpha,10alpha-epoxy-17alpha-ethoxymethyl-17beta-methoxy-estr-9(11)-ene-3,3-dimethyl ketal is obtained as colorless oil, which is used directly in the next step.

d) 0.15 ml of dibromoethane and then 4.95 g of 1-(4-bromophenyl)-ethanon-1,1-ethylene ketal in 30 ml of abs. THF is instilled in 486 mg of magnesium in 5 ml of abs. ether under argon. It is stirred for 3 hours at 50° C. internal temperature, cooled to 0° C. and 170 mg of CuCl is added. After 20 more minutes, 940 mg of 5alpha,10alpha-epoxy-17alpha-ethoxymethyl-17beta-methoxy-estr-9(11)-ene-3,3-dimethyl ketal in 20 ml THF is instilled. It is stirred for 2 hours at room temperature, the batch is decomposed with aqueous ammonium chloride solution and extracted with ethyl acetate. The organic phase is washed neutral, dried on Na$_2$SO$_4$ and evaporated under vacuum. The crude product is purified by column chromatography on 60 g of aluminum oxide (alkaline) with a benzene/ethyl acetate gradient. 700 mg of 3,3-dimethoxy-11beta-[4-(1,1-ethylenedioxyethyl)-phenyl]-17alpha-ethoxymethyl-17beta-methoxy-estr-9-en-5alpha-ol is obtained as colorless oil, which is further processed directly.

e) 700 mg of 3,3-dimethoxy-11beta-[4-(1,1-ethylenedioxyethyl)-phenyl]-17alpha-ethoxymethyl-17beta-methoxy-estr-9-en-5alpha-ol is stirred in 20 ml of dilute acetic acid (70%) for 20 hours at room temperature. After addition of water, it is extracted with ethyl acetate, the organic phase is washed with dilute aqueous NaOH and water, dried on Na$_2$SO$_4$ and evaporated under vacuum. The crude product is purified by preparative layer chromatography on silica gel 60 with the mobile solvent mixture benzene/acetone 9:1 (v/v). 290 mg of 11beta-(4-acetylphenyl)-17alpha-ethoxymethyl-17beta-methoxy-estra-4,9-dien-3-one is obtained.

Mp: 134° C. to 137° C. (acetone/ether)

$[\alpha]_D$: +180° (CHCl$_3$)

EXAMPLE 9

11beta-(4-Acetylphenyl)-17beta-methoxy-17alpha-propoxymethyl-estra-4,9-dien-3-one a) A sodium naphthalide solution (produced from 375 mg of sodium and 1.9 g of naphthalene in 100 ml of THF) is instilled in 3.9 g of 3,3-dimethoxy-17alpha-propoxymethyl-estra-5(10),9(11)-dien-17beta-ol in 30 ml of THF until a dark green coloring remains, and the alcoholate is formed.

b) After 30 minutes stirring at 20° C., 8 ml of methyl iodide is slowly instilled in the solution and is stirred for 3 more hours at room temperature. After addition of aqueous NH$_4$Cl solution is extracted several time with ethyl acetate. The organic phase is washed neutral, dried on K$_2$CO$_3$ and Na$_2$SO$_4$ and the solvent is evaporated under vacuum. The crude product is purified by column chromatography on 140 g of aluminum oxide (alkaline) with a benzene/ethyl acetate gradient. 3.56 g of 17beta-methoxy-17alpha-propoxymethyl-estra- 5(10),9(11)-diene-3,3-dimethyl ketal is obtained as colorless oil, which is used directly in the next step.

c) 1 g of NaHCO₃, 2.5 g of NaH₂PO₄, 4.5 ml of H₂O₂ and 1.5 g of chloral hydrate are added to 3.56 g of 11beta-methoxy-17alpha-propoxymethyl-estra-5(10),9(11)-diene-3,3-dimethyl ketal in 20 ml of methylene chloride. It is stirred for about 3.5 hours until complete reaction at room temperature, water is added and it is extracted with methylene chloride. The organic phase is successively washed with aqueous bisulfite solution, K₂CO₃ solution and water, dried on Na₂SO₄ and evaporated under vacuum. The crude product is purified by column chromatography on 120 g of aluminum oxide (alkaline) with a benzene/ethyl acetate gradient. 2.45 g of 5alpha,10alpha-epoxy-17beta-methoxy-17alpha-propoxymethyl-estr-9(11)-ene-3,3-dimethyl ketal is obtained as colorless oil, which is used directly in the next step.

d) 0.2 ml of dibromoethane and 5.7 g of 1-(4-bromophenyl)-ethanon-1,1-ethylene ketal in 30 ml of abs. THF are successively added so 560 mg of magnesium in 5 ml of abs. ether. It is stirred for 3 hours at 50° C. internal temperature, cooled to 0° C. and 220 mg of CuCl is added. After another 20 minutes, 2.45 g of 5alpha,10alpha-epoxy-17beta-methoxy-17alpha-propoxymethyl-estr-9(11)-ene-3,3-dimethyl ketal in 40 ml of abs. THF is instilled. It is stirred for 3 hours at room temperature, decomposed with aqueous NH₄Cl solution and extracted with ethyl acetate. It is washed colorless and neutral, dried on Mg₂SO₄ and concentrated by evaporation. The crude product is purified on 100 g of aluminum oxide (alkaline) with a benzene/ethyl acetate gradient. 1.5 g of 3,3-dimethoxy-11beta-[4-(1,1-ethylenedioxyethyl)-phenyl]-17beta-methoxy-17alpha-propoxymethyl-estr-9-en-5alpha-ol is obtained as colorless oil, which is used directly in the next step.

e) 20 ml of dilute acetic acid (70%) is added to 1.5 g of 3,3-dimethoxy-11beta-[4-(1,1-ethylenedioxyethyl)-phenyl-17beta-methoxy-17alpha-propoxymethyl-estr-9-en-5alpha-ol and the mixture is stirred for 4 hours at room temperature. After addition of water, it is extracted with ethyl acetate, the organic phase is washed with aqueous diluted NaOH and water, dried on Na₂SO₄ and evaporated under vacuum. The crude product is recrystallized from ether/acetone/hexane. 790 mg of 11beta-(4-acetylphenyl)-17beta-methoxy-17alpha-propoxymethyl-estr-4,9-dien-3-one is obtained.

Mp: 118° C. to 120° C.

$[\alpha]_D = +160°$ (CHCl₃)

EXAMPLE 10

Steps a) to c) as Under example 7.

0.15 ml of dibromoethane and then 5 g of p-bromodimethyl-aniline in 15 ml of abs. THF is instilled in 850 mg of magnesium in 10 ml of abs. THF under argon. It is stirred for 3 hours at 50° C. internal temperature, cooled to −20° C. and 200 mg of CuCl is added. After 20 more minutes, 1.72 g of 5alpha,10alpha-epoxy-17beta-methoxy-17alpha-methoxymethyl-estr-9(11)-ene-3,3-dimethyl ketal in 15 ml of THF is instilled. It is stirred for 1 hour at 10° C. to 15° C. and then at room temperature, the batch is decomposed with aqueous ammonium chloride solution and extracted with ether. The organic phase is washed neutral, dried on Na₂SO₄ and evaporated under vacuum. The crude product is purified by column chromatography on 70 g of aluminum oxide (alkaline) with a benzene/ethyl acetate gradient. 1.1 g of 3,3-dimethoxy-11beta-(4-dimethylaminophenyl)-17beta-methoxy-17alpha-methoxymethyl-estr-9-en-5alpha-ol is obtained as colorless oil, which is further processed directly.

e) 700 mg of 3,3-dimethoxy-11beta-(4-dimethylaminophenyl)-17beta-methoxy-17alpha-methoxymethyl-estr-9-en-5alpha-ol is stirred in 20 ml of dilute acetic acid for 20 hours at room temperature. After addition of water, it is extracted with ethyl acetate, the organic phase is washed with diluted aqueous NaOH and water, dried on Na₂SO₄ and evaporated under vacuum. After repeated preparative layer chromatography on aluminum oxide (neutral) and silica gel PF₂₅₄, 420 mg of 11beta-(4-dimethylaminophenyl)-17beta-methoxy-17alpha-methoxymethyl-estra-4,9-dien-3-one is obtained as foam.

$[\alpha]_D = +167°$ (CHCl₃)

¹H NMR (CDCl₃, TMS)

δ(ppm): 0.59 (s, 3H, H 18); 2.95 (s, 6H, N(CH₃)₂); 3.26 (s, 3H, 17beta OCH₃); 3.41 (s. 3H, 17alpha-CH₂OCH₃); 3.30–3.64 (m, 2H, ABX system, 17alpha-C$\underline{H}_2$OC$\underline{H}_3$); 4.30 (d, J=7 Hz, 1H, H-11); 5.75 (s, 1H, H-4); 6.60–7.06 (m, 4H, AA'BB' system of the aromatic).

We claim:

1. An 11β-aryl-gona-4,9-diene of formula I

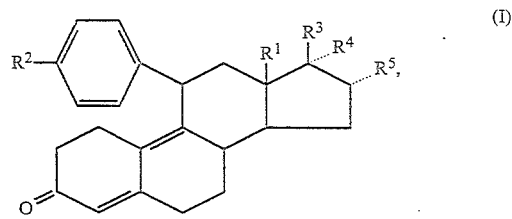

R³ is methoxy;

R⁴ is propinyl or methoxymethyl; and

R⁵ is H.

2. A compound of claim 1, wherein R⁴ is propinyl.

3. 17β-methoxy,17α-methoxymethyl-11β-(4-acetylphenyl)-estra-4,9-diene-3-one, a compound of claim 1.

4. A pharmaceutical preparation, comprising an effective amount of a compound of claim 1 and a pharmaceutically acceptable excipient.

5. A method of inducing abortion, comprising administering to a patient in need of such treatment an effective amount of a compound of claim 1.

* * * * *

UNITED STATES PATENT AND TRADEMARK OFFICE
CERTIFICATE OF CORRECTION

PATENT NO. : 5,407,928
DATED : April 18, 1995
INVENTOR(S) : Helmut KASCH et al.

It is certified that error appears in the above-indentified patent and that said Letters Patent is hereby corrected as shown below:

Claim 1; column 22, line 45: Insert -- Wherein $R^1$ is methyl; $R^2$ is acetyl; --.

Signed and Sealed this

Fifteenth Day of August, 1995

Attest:

BRUCE LEHMAN

Attesting Officer  Commissioner of Patents and Trademarks